United States Patent
Athanikar

(10) Patent No.: US 6,616,938 B2
(45) Date of Patent: Sep. 9, 2003

(54) METHOD OF MAKING CHEWING GUM CONTAINING COLLOIDAL BISMUTH SUBCITRATE

(75) Inventor: Narayan K. Athanikar, Irvine, CA (US)

(73) Assignee: Josman Laboratories, Inc., Irvine, CA (US)

(*) Notice: Subject to any disclaimer, the term of this patent is extended or adjusted under 35 U.S.C. 154(b) by 0 days.

(21) Appl. No.: 09/875,843

(22) Filed: Jun. 6, 2001

(65) Prior Publication Data

US 2001/0036445 A1 Nov. 1, 2001

Related U.S. Application Data

(63) Continuation of application No. 09/072,523, filed on May 4, 1998, now Pat. No. 6,258,376, which is a continuation-in-part of application No. 08/741,781, filed on Nov. 1, 1996, now Pat. No. 5,834,002, which is a continuation-in-part of application No. 08/385,060, filed on Feb. 7, 1995, now abandoned.

(30) Foreign Application Priority Data

May 2, 1994 (JP) .................................... 6-93518

(51) Int. Cl.⁷ ........................... A61K 9/68; A61K 33/24
(52) U.S. Cl. ...................................... 424/440; 424/653
(58) Field of Search ............................... 424/440, 653; 514/925–927, 948

(56) References Cited

U.S. PATENT DOCUMENTS

| | | |
|---|---|---|
| 3,011,949 A | 12/1961 | Bilotti |
| 3,247,051 A | 4/1966 | Leebrick |
| 3,352,689 A | 11/1967 | Bilotti |
| 3,577,533 A | 5/1971 | Rider |
| 3,651,208 A | 3/1972 | Lauster |
| 3,824,006 A | 7/1974 | Voit |
| 3,929,449 A | 12/1975 | Hedrich |
| 3,943,258 A | 3/1976 | Bahoshy et al. |
| 3,973,041 A | 8/1976 | DuRoss |
| 3,982,023 A | 9/1976 | Bahoshy et al. |
| 4,016,268 A | 4/1977 | Goldenberg et al. |
| 4,055,655 A | 10/1977 | Maurer et al. |
| 4,118,480 A | 10/1978 | Williams |
| 4,153,685 A | 5/1979 | Serfontein |
| 4,180,473 A | 12/1979 | Maurer et al. |
| 4,208,431 A | 6/1980 | Friello et al. |
| 4,217,368 A | 8/1980 | Witzel et al. |
| 4,514,421 A | 4/1985 | Herschler |
| 4,652,444 A | 3/1987 | Maurer |
| 4,670,245 A | 6/1987 | Vasquez et al. |
| 4,680,309 A | 7/1987 | Maurer |
| 4,800,083 A | 1/1989 | Hom et al. |
| 4,801,454 A | 1/1989 | Coveney |
| 4,801,608 A | 1/1989 | Bos et al. |
| 4,822,597 A | 4/1989 | Faust et al. |
| 4,879,116 A | 11/1989 | Fox et al. |
| 4,917,899 A | 4/1990 | Geoghegan et al. |
| 4,940,695 A | 7/1990 | Coveney et al. |
| 4,956,386 A | 9/1990 | McLoughlin et al. |

(List continued on next page.)

FOREIGN PATENT DOCUMENTS

| | | |
|---|---|---|
| AU | 262452 | 3/1963 |
| AU | 65846 | 5/1967 |
| DE | 1963496 | 6/1971 |
| DE | 2012187 | 9/1971 |
| DE | 31 27 639 | 8/1982 |
| EP | 0206627 B1 | 12/1968 |
| EP | 0075992 A1 | 4/1983 |
| EP | 0206626 A2 | 12/1986 |
| EP | 0403048 A2 | 6/1989 |
| EP | 0367484 A1 | 5/1990 |
| EP | 0375063 A1 | 6/1990 |
| EP | 0377477 A1 | 7/1990 |
| EP | 0437294 A1 | 7/1991 |
| FR | 070408 | 3/1968 |
| FR | 102365 | 7/1968 |
| FR | 101072 | 12/1968 |
| GB | 1144915 | 3/1964 |
| GB | 1107655 | 3/1968 |
| GB | 1478742 | 7/1977 |
| GB | 2 195 248 | 4/1988 |
| GB | 2195890 A | 4/1988 |
| GB | 2195891 A | 4/1988 |
| GB | 2195892 A | 4/1988 |
| JP | 8-20543 | 1/1996 |
| WO | WO86/05981 | 10/1986 |
| WO | WO91/03241 | 3/1991 |
| WO | WO92/01457 | 2/1992 |
| WO | WO 97/00668 | 1/1997 |

OTHER PUBLICATIONS

Abstracts of Papers *Gastroenterology*, 1986, vol. 88, No. 5, part 2, pp. 1434, 1585, 1599, 1620.
Abstracts of Papers *Gastroenterology*, vol. 90, No. 5, Part 2, p. 1580.
Abstracts of Papers, *Gastroenterology*, vol. 92, No. 5, Part 2, p. 1518.
"Aldefur" *Unlisted Drugs* (Nov. 1970) vol. 22, No. 11, p. 163b.
"Corygest" *Unlisted Drugs* (Mar. 1982) vol. 34, No. 3, p. 38.
"Uplex 59051B" *Rote List* (1976).
1994 Annual Report for Applied Microbiology, Inc.; distributed with notice of Annual Shareholders Meeting which was mailed Feb. 1995.

(List continued on next page.)

*Primary Examiner*—Edward J. Webman
(74) *Attorney, Agent, or Firm*—Brinks Hofer Gilson & Lione; Gregory H. Zayia

(57) ABSTRACT

The invention provides a method of making a chewing gum composition containing a water soluble bulk portion, a water insoluble chewing gum base portion, a flavoring agent, and bismuth-containing compounds. The invention provides a method of making a bismuth-containing gum which when chewed multiple times per day, over the period of two weeks, is effective in reducing peptic ulcers by eradicating *H. pylori*. The chewing gum is also effective in eliminating forms of halitosis. The chewing gum does not have undesirable side effects, such as unpleasant taste and poor chewing characteristics.

18 Claims, No Drawings

U.S. PATENT DOCUMENTS

| | | | |
|---|---|---|---|
| 4,965,382 | A | 10/1990 | Furlan |
| 4,975,270 | A | 12/1990 | Kehoe |
| 5,002,776 | A | 3/1991 | Geoghegan et al. |
| 5,013,560 | A | 5/1991 | Stentz et al. |
| 5,017,367 | A | 5/1991 | Stojkoski |
| 5,093,342 | A | 3/1992 | Tomoi et al. |
| 5,192,752 | A | 3/1993 | Chapura et al. |
| 5,196,205 | A | 3/1993 | Borody |
| 5,256,684 | A | 10/1993 | Marshall |
| 5,260,304 | A | 11/1993 | Gergely et al. |
| 5,264,222 | A | 11/1993 | Groenendaal et al. |
| 5,286,492 | A | 2/1994 | Dettmar |
| 5,286,497 | A | 2/1994 | Hendrickson et al. |
| 5,294,433 | A | 3/1994 | Singer et al. |
| 5,304,540 | A | 4/1994 | Blackburn et al. |
| 5,324,750 | A | 6/1994 | Lincoln et al. |
| 5,334,582 | A | 8/1994 | Blackburn et al. |
| 5,352,679 | A | 10/1994 | Ferrieri et al. |
| 5,368,845 | A | 11/1994 | Gaffar et al. |
| 5,372,815 | A | 12/1994 | Hodutu |
| 5,385,739 | A | 1/1995 | Debregeas et al. |
| 5,403,830 | A | 4/1995 | Place |
| 5,425,948 | A | 6/1995 | Olivieri |
| 5,466,681 | A | 11/1995 | Krivan et al. |
| 5,476,669 | A | 12/1995 | Borody |
| 5,514,660 | A | 5/1996 | Zopf et al. |
| 5,536,510 | A | 7/1996 | Tyrpin et al. |
| 5,559,096 | A | 9/1996 | Edwards et al. |
| 5,601,848 | A | 2/1997 | Marshall |
| 5,604,212 | A | 2/1997 | Blank |
| 5,788,974 | A | 8/1998 | D'Amico et al. |
| 5,804,549 | A | 9/1998 | Blackburn et al. |
| 5,834,002 | A | 11/1998 | Athanikar |
| 5,840,281 | A | 11/1998 | Gaffar et al. |

OTHER PUBLICATIONS

Abraham et al. "Helicobacter pylori in its lair: a role in ulcer recurrance?" *Indian Journal of Gastroenterology* (1990) vol. 9, No. 4, pp. 265–269.

Andersen et al. "Campylobacter pylori in Peptic Ulcer Disease. II. Endoscopic Findings and Culltivation of C. pylori." *Scand. J. Gastroenterol.* (1988), pp. 760–764.

Axon "[chapter] V. Helicobacter pylori therapy: Effect on peptic ulcer disease" *Journal of Gastroenterology and Hepatology* (1991) vol. 6, pp. 131–137.

Axon "Campylobacter pylori—Therapy Review" *Scand J Gastroenterol.*, (1989) vol. 24, supp. 160, pp. 35–38.

Bader. "The Safety Profile of De–Nol®" *Digestion*, vol. 37, supp. 2 (1987) pp. 53–59.

Beil et al. "Studies on the Mechanism of Action of Colloidal Bismuth Subcitrate" *Pharmacology*, (1993) vol. 47, pp. 135–144.

Benet "Safety and Pharmacokinetics: Colloidal Bismuth Subcitrate", *Scand. J. Gastroenterol* (1989) vol. 26, supp. 185, pp. 29–35.

Bettarello "Anti–ulcer therapy. Past to present" *Digestive Diseases and Sciences* (Nov. 1985) vol. 30, supp. 11, pp. 36S–42S.

Bianchi Porro et al. "Comparison of tripotassium dicitrato bismuthate (TDB) tablets and ranitidine in healing and relapse of duodenal ulcers" *The British Society of Gastroenterology* (1984) vol. 25, p. A565, No. F51 [abstract only].

Bianchi Porro et al. "Maintenance therapy with colloidal bismuth subcitrate in duodenal ulcer disease" *Digestion* (1987) vol. 37, supp. 2, pp. 47–52.

Bianchi Porro et al. "Relapse Rates in Duodenal Ulcer Patients Formerly Treated with Bismuth Subcitrate or Maintained with Cimetidine" *The Lancet* (1984) vol. 2, p. 698.

"Bismosal Mixture Cholera Infantum, Norwich" (1918) [advertisement].

"Stomach Upset" (1951) [advertisement].

Blaser et al. "Campylobacter Enteritis" *New England Journal of Medicine* (1981) vol. 306, pp. 1444–1452.

Bornkessel "Helicobacter pylori bei Ulkuserkrankungen" *Arneimitteltherapiel* (13.Jahrgang/Heft1/1995) pp. 17–19 [in German].

Borody et al. "High Efficacy, Low Dose Triple Therapy (TT) for Helicobacter pylori (HP)" *Gastroenterology* (1992) vol. 102, No. 4, Part 2, pp. A44 [abstract only].

Börsch et al. "Helicobacter pylori" *Pharmacology of peptic ulcer disease* (1991) pp. 106–147.

Bosy et al. "Relationship of Oral Malodor to Periodontitis: Evidence of Independence in discrete subpopulations" *J. Periodontol* (1992) vol. 65, No. 1 pp. 37–46.

Bouvet "Bismuth salts used in gastro–enterology. Data of animal investigations" *Ann. Pharm. Fr* (1980), vol. 38, pp. 447–454 [in French with English summary].

Boyd et al. "Recurrent ulcer disease" *Gastroenterology Clinics of America. Helicobacter pylori Infection* (Mar. 1993) vol. 22, No. 1, pp. 14–42.

Breuer et al. "Epidemiologie und Pathogenese der Helicobacter pylori–infektion" *GASTRO–LIGO Report* (Mar./Apr. 1994) pp. 1–5 [in German].

Brogden et al. "Tri–potassium di–citrato bismuthate: a report of its pharmacological properties and therapeutic efficacy in peptic ulcer" *Drugs* (1976) vol. 12, pp. 401–411.

Chemical Abstracts Service (1983) vol. 98, p. 384, No. 221850c [abstract only].

Coghill et al. "The ultrastructural localization of De–Nol (colloidal tripotassium dicitrato–bismuthate–TDB) in the upper gastrointestinal tract of man and rodents following oral and instrumental administration" *Chemical Abstract Service* (1983) vol. 98, p. 15, No. 172475y [abstract only].

Colson "The treatment of chronic colitis and colopathies by a new association of bismuth, mucilage, oxyquinoline and meprobamate" *Revue des corps de santé des Armées* (1966) vol. 7, No. 2, p. 319–334 [English translation of the French article].

Correa et al. "Helicobacter pylori and gastric cancer" *Helicobacter pylori and gastroduodenal disease* (1992) pp. 157–164.

De Boever et al. "Assessing the Contribution of Anaerobic Microflora of the Tongue to Oral Malodor" *JADA*, (Oct. 1995) vol. 126, pp. 1384–1393.

Deák et al. "A controlled clinical trial with De–Nol (tripotassium dicitrato bismuthate) in patients with gastric ulcer" *Int J. Tissue Reac* (1983) vol. 5, No. 4, pp. 397–401.

Desai et al. "Dental Plaque: A Permanent Reservoir of Helicobacter Pylori?" *Scand. J. Gastroenterol* (1991) vol. 26, pp. 1205–1208.

Dixon "[chapter] IV. Helicobacter pylori and peptic ulceration: histopathological aspects" *Journal of Gastroenterology and Hepatology* (1991) vol. 6, pp. 125–130.

Dobrilla et al. "Influence of ulcer healing agents on ulcer relapse after discontinuation of acute treatment: a pooled estimate of controlled clinical trials" *Gut* (1988) vol. 29, pp. 181–187.

Dunn "The role of Helicobacter pylori in gastrointestinal diseases" *Gastrointestinal Disease Management* (Aug. 1991), pp. 173–182.

Eberhardt et al. "Effect of oral bismuthsubsalicylate on Campylobacter pyloridis and on duodenal ulcer" *Gastroenterology* (May 1987) vol. 92, No. 5, p. 1379 [abstract only].

Eidt et al. "The significance of *Helicobacter pylori* in relation to gastric cancer and lymphoma" *European Journal of Gastroenterology & Hepatology* (1995) vol. 7, No. 4, pp. 318–321.

Forman et al. "An international asssociation between Helicobacter pylori infection and gastric cancer" *The Lancet* (May 29, 1993) vol. 341, No. 8857, pp. 1359–1362.

Forman et al. "H. pylori and gastric cancer: the significance of the problem" *Helicobacter pylori Basic Mechanisms to Clinical Cure.* (1994), pp. 461–468.

Freedberg et al. "The Presence of Spirochetes in Human Gastric Mucosa" *American Journal of Digestive Diseases* (1940) vol. 7, pp. 443–445.

Gisselbrecht et al. "Treatment of constipation and colitis by the association of bismuth subnitrate and Karaya gum" *Lyon Med.*, (1970) vol. 223, No. 18, pp. 951–958 [French article and English translation].

Goh et al. "Helicobacter pylori Infection and Non–Ulcer Dyspepsia: The Effect of Treatment with Colloidal Bismuth Subcitrate", *Scand. J. Gastroenterol* (1991) vol. 26, pp. 1123–1131.

Goldenberg et al. "Protective Effects of Pepto–Bismol Liquid on the Gastric Mucosa of Rats" *Gastroenterology* (1975), vol. 69, pp. 636–640.

Goodman. *The Pharmacological Basis of Therapeutics.* Fifth edition. (1975) pp. 930, 997–998.

Goodwin "Taxonomy of Helicobacter pylori and related bacteria" *Helicobacter pylori, gastritis and peptic ulcer* (1990) pp. 1–8.

Goodwin et al. "The minimum inhibitory and bactericidal concentrations of antibiotics and anti–ulcer agents against Campylobacter pyloridis" *J. Antimicrobial Chemotherapy* (1986) vol. 17, pp. 309–314.

Gorbach "Bismuth therapy in gastrointestinal diseases" *Gastroenterology* (Sep. 1990) vol. 99, No. 3, pp. 863–875.

Graham "Helicobacter pylori: human pathogen or simply and opportunist?" *The Lancet* (Apr. 29, 1995) vol. 345, pp. 1095–1097.

Graham et al. "Factors influencing the eradication of Helicobacter pylori with triple therapy" *Gastroenterology* (1992) vol. 102, pp. 493–496.

Gregory "The Effect of Tri–Potassium Di–citrato Bismuthate on the Duodenal Mucosa During Ulceration" *S.A. Medical Journal* (1982) vol. 62, pp. 52–55.

Hamilton et al. "Effects of tripotassium dicitrato–bismuthate (TDB) tablets or cimetidine in the treatment of duodenal ulcer" *Gut* (Dec. 1983) vol. 24, No. 12, pp. 1148–1151.

He et al. "Cytoprotection of Furazolidone in Resistant–Soakage Gastric Ulcers in Rats" *Jinau Liyi Xuebao* (1984) vol. 4, pp. 55–59.

Héraud et al. "Therapeutical trial of an association of an insoluble bismuth salt and a Karaya gum in gastro–intestinal pathology" *Lille Medical, 3rd Series,* (1969) vol. XIV, No. 6, supplement, pp. 677–679 [French article with English translation].

Hislop et al. "Histological Improvement of Active Chronic Gastritis in Patients Treated with De–Nol", presented at a meeting of the Gastroenterological Society of Australia (Mar. 11–14, 1984), *Gastroenterological Society of Australia* (Dec. 1984) p. 907 [abstract only].

Hosking et al. "Duodenal Ulcer Healing by Eradication of Helicobacter pylori without anti–acid treatment: randomised controlled trials" *The Lancet* (1994) vol. 343, pp. 508–510.

Jensen et al. "Chewing gum and lozenges as delivery systems for noscapine" *Acta Pharm. Nord* (1991) vol. 3, No. 4, pp. 219–222.

Jones et al. "Acid suppression in duodenal ulcer: a meta–analysis to define optical dosing with antisecretory drugs" *Gut* (1987), vol. 28, pp. 1120–1127.

Kleinberg et al. "Salivary and Metabolic factors involved in oral malodor formation" *J. Periodontol* (1992) vol. 63, No. 9, pp. 768–775.

Konturek et al. "Advances in the understanding of the mechanism of cytoprotective action by colloidal bismuth subcitrate" *Scand. J. Gastroenterol* (1986) vol. 21, supp. 122, pp. 6–10.

Konturek et al. "Studies on the gastroprotective and ulcer–healing effects of colloidal bismuth subcitrate" *Digestion* (1987) vol. 37, supp. 2, pp. 8–15.

Koo et al. "Selective Coating of Gastric Ulcer by Tripotassium Dicitrato Bismuthate in the Rat", *Gastroenterology* (May 1982) vol. 82, No. 5 pp. 864–870.

Lambert, I. *The Lancet* (Apr. 10, 1993) vol. 341, p. 957 [letter only].

Lambert, J.R. "Clinical Indications and Efficacy of Colloidal Bismuth Subcitrate" *Scand. J. Gastroenterol* (1991) vol. 26, supp. 185, pp. 13–21.

Lambert, J.R. et al. "Helicobacter pylori" *Mechanisms of Injury, Protection and Repair of the Upper Gastrointestinal Tract* (1991), pp. 19–28.

Lambert, T. et al. "Susceptibility of Campylobacter pyloridis to 20 Antimicrobial Agents" *Antimicrobial Agents and Chemotherapy* (Sep. 1986) vol. 30, No. 3, pp. 510–511.

Lane et al. "Tripotassium dicitrato–bismuthate tablets v liquid in the treatment of duodenal ulcers" *N Z Med J* (Mar. 27, 1985) vol. 98, No. 775, pp. 191–192.

Langenberg et al. "Campylobacter–like Organisms in the Stomach of Patients and Healthy Individuals" *The Lancet* (Jun. 16, 1984) vol. 1, pp. 1348–1349; 1336–1337.

Lashner et al. "Testing Nicotine Gum for Ulcerative Colitis Patients" *Digestive Diseases and Sciences* (Jul. 1990), vol. 35, No. 7, pp. 827–832.

Lee F.I. et al. "Comparison of Tri–potassium D–citrato Bismuthate Tablets with Ranitidine in Healing and Relapse of Duodenal Ulcers" *The Lancet* (Jun. 8, 1985) vol. 1, pp. 1299–1301.

Lee, S.P. "The Mode of Action of Colloidal Bismuth Subcitrate" *Scand. J. Gastroenterol* (1991) vol. 26, supp. 1985, pp. 1–6.

Lee, S.P. et al. "Increased healing of gastric and duodenal ulcers in a controlled trial using tripotassium dicitrato–bismuthate" *Med. J. Aust* (May 28, 1977) vol. 1, No. 22, pp. 808–812.

Lee et al. "A freeze–injured skin graft model for the quantitative study of basic fibroblast growth factor and other promoters of angiogenesis in wound healing" *British Journal of Plastic Surgery* (1994) vol. 47, pp. 349–359.

Logan et al. "One week eradication regimen for helicobacter pylori" *The Lancet* (1991) vol. 338, pp. 1249–1252.

Lorber "Antipeptic agents, carbenoxolone, and mucosal coating agents: status report" *Chemical Abstracts Service* (1981) vol. 94, p. 93, No. 168025b [abstract only].

Lu et al. "Effect of Furaxon and It [sic] Analogs on Gastrointestinal Propulsion in Mice" *Beijing Yixueyuan Xuebao* (1983) vol. 15, pp. 185–187.

Marcheggiano, et al. "Campylobacter–Like Organisms (CLOs) Gastritis and Peptic Ulcer", (1986) p. 1533, [abstract only].

Marshall "Helicobacter pylori" *The American Journal of Gastroenterology* (1994) vol. 89, No. 8, pp. S116–S128.

Marshall "Treatment Strategies for Helicobacter pylori Infection" *Gastroenterology Clinics of America. Helicobacter pylori infection.* vol. 22, No. 1, pp. 186–195.

Marshall et al. "Histological Improvement of Active Chronic Gastritis in Patients Treated with De–Nol" *Australia & New Zealand J. of Medicine* (Dec. 1984) vol. 14, p. 907.

Marshall et al. "Pyloric Campylobacter Infection and Gastroduodenal Disease" *The Medical Journal of Australia* (Apr. 15, 1985) vol. 142 pp. 439–444.

Marshall et al. "Pyloric Campylobacter Serology" *The Lancet* (Aug. 4, 1984) vol. 2, p. 281 [letter only].

Marshall et al. "Spiral bacteria in the human stomach: a common finding in patients with gastritis and duodenal ulcer" *Campylobacter II, Proceedings of the Second International Workshop on Campylobacter Infections* (1983) pp. 11–12.

Marshall et al. "Unidentified Curved Bacilli in the Stomach of Patients with Gastritis and Peptic Ulceration" *The Lancet* (Jun. 15, 1984) vol. 1, pp. 1311–1315.

Marshall "Perspective—Campylobacter pyloridis and Gastritis" *J. of Infectious Diseases* (1986) vol. 153, pp. 650–657.

Martin et al. "Difference in relapse rates of duodenal ulcer after healing with cimetidine or tripotassium dicitrato bismuthate" *The Lancet* (Jan. 3, 1981), pp. 7–10.

Matuszewska et al. "Acidic Fibroblast Growth Factor: Evaluation of Topical Formulations in a Diabetic Mouse Wound Healing Model" *Pharmaceutical Reasearh* (1994), vol. 11, No. 1 pp. 65–71.

McDowell, et al. "Diagnosing and Treating Halitosis" *JADA*, vol. 124 (Jul. 1993) pp. 55–64.

McLean et al. "Microbes, Peptic Ulcer and Relapse Rates with Different Drugs" *The Lancet* (Sep. 1, 1984) vol. 2, pp. 525–526.

McNulty et al. "Campylobacter pyloridis and associated gastritis: Investigator blind, placebo controlled trial of bismuth salicylate and erthyromycin ethylsuccinate" *British Medical Journal*, (Sep. 13, 1986) vol. 293, pp. 645–649.

McNulty et al. "Spiral Bacteria of the Gastric Antrum" *The Lancet* (May 12, 1984) vol. 1, p. 1068.

McNulty et al. "Successful therapy of Campylobacter pyloridis gastrinitis" *Abstracts of Papers* (May 1986), p. 1547 [abstract only].

McNulty et al. "Susceptibility of Clinical Isolates of Campylobacter pyloridis to 11 Antimicrobial Agents" *Antimicrobial Agents and Chemotherapy* (Dec. 1985) vol. 28, No. 6, pp. 837–838.

McNulty et al. "Rapid Diagnosis of Campylobacter–Associated Gastritis" *The Lancet* (1985) pp. 1443–1444.

Morris et al. "Ingestion of Campylobacter pyloridis causes gastritis and raised fasting gastric pH" *The American Journal of Gastroenterology* (1987), vol. 82, No. 3, pp. 192–199.

Mustofa et al. "Pharmacokinetics of metronidazole in saliva" *International Journal of Clinical Pharmacology, Therapy and Toxicology* (Dec. 1991) vol. 29, No. 12, pp. 474–478.

Nakao, et al. "Antibacterial Properties of Lansoprazole Alone and in Combination with Antimicrobial Agents Against Helicobacter pylori" *Eur. J. Clin. Microbiol. Infect. Dis.*, vol. 14, No. 5 (1995) pp. 391–399.

Nakao. "Antibacterial Properties of Lansoprazole Alone and in Combination with Antimicrobial Agents Against Helicobacter pylori" *J. Clin. Gastroenterol.*, vol. 20, supp. 1 (1995) pp. S32–S37.

Navarranne "Treatment of spasmodic and psychosomatic colopathies by a cicatrisant, antiseptic and anziolytic medication combination" *Therapie* (1967) vol. XXII, pp. 419–426.

Nguyen et al. "Detection of Helicobacter pylori in Dental Plaque by Reverse Transcription–Polymerase Chain Reaction" *Journal of Clinical Microbiology* (Apr. 1993) vol. 31, No. 4, pp. 783–787.

Norfleet "Helicobacter halitosis" *J. Clin. Gastroenterol.*, (1993) vol. 16, No. 3 [letter only].

O'Connor et al. "Vitamin C in the human stomach; relation to gastric pH, gastroduodenal disease and possible sources" *Gut* (1989) vol. 30, pp. 436–442.

Olsson et al. "H. pylori in dental plaques" *The Lancet* (Apr. 10, 1993) vol. 341, pp. 956–957.

Parsonnet "Helicobacter pylori infection. Helicobacter pylori and gastric cancer" *Gastroenterology Clinics of North America* (Mar. 1993) vol. 22, No. 1 pp. 89–104.

*Physicians Desk Reference for Nonprescription Drugs* (1985) p. 646.

Rauws, "Cure of duodenal ulcer associated with eradication Helicobacter pylori" *The Lancet*, vol. 335, pp. 1233–1235.

Rauws, et al. "Campylobacter pyloridis–Associated Chronic Active Antral Gastritis. A prospective study of its prevalence and the effects of antibacterial and antiulcer treatment" *Gastroenterology.* vol. 94 (1988) pp. 33–40.

Recavarren–Arce et al. "Helicobacter pylori and progressive gastric pathology that predisposes to gastric cancer" *Scand. J. Gastroenterol* (1991) vol. 26, supp. 181, pp. 52–57.

Reed et al. "Effect of ascorbic acid on the intragastric environment in patients at increased risk of developing gastric cancer" *Iarc Scientific Publications* (1991) vol. 105, pp. 139–142.

Reynolds (editor) *Martindale The Extra Pharmacopoeia* $28^{th}$ Ed (1982) pp. 927–930.

Rosenberg et al. "Day–Long Reduction of Oral Malodor by a Two–Phase Oil: Water Mouthrinse as compared to chlorhexidine and placebo rinses" *J. Periodontol* (1982) vol. 63, No. 1, pp. 39–43.

Sakaki et al. "An endoscopic study on relationship between Helicobacter pylori infection and endoscopic gastric ulcer scars" *Digestive Diseases and Sciences* (May 1995) vol. 40, No. 5, pp. 1087–1092.

Schmitt. "New Methods of Delivery of Amphotericin B" *Clinical Infectious Diseases.* vol. 17, supp. 2 (1993), pp. S501–506.

Schorah et al. "Gastric juice ascorbic acid: effects of disease and implications for gastric carcinogenesis" *Clin Nutr* (1991) vol. 53, pp. 287S–293S.

Seppälä, "H pylori and gastric ulcer disease" *Helicobacter pylori Basic Mechanisms to Clinical Cure* (1994) pp. 429–436.

Shirokova et al. "The Use of Metronidazole in Treatment of Patients with Ulcerative Disease" *Klin. Med.–(Mosk)* (1981) vol. 59, pp. 48–50.

Shreeve et al. "Comparison of cimetidine and tripotassium dicitrato bismuthate in healing and relapse of duodenal ulcers" *Digestion* (1983) vol. 28, No. 2, pp. 96–101.

Sipponen et al. "Long–term consequences of H. pylori infection: time trends in H. pylori gastritis, gastric cancer and peptic ulcer disease" *Helicobacter pylori Basic Mechanisms to Clinical Cure* (1994) pp. 372–380.

Skirrow "Report on the Session: Infections due to campylobacters other than *C. jejuni* and *C. coli.*" *Campylobacter ii, Proceedings of the Second International Workshop on Campylobacter Infections* (1983) pp. 5–10.

Sobala et al. "Acute Helicobacter pylori infection: clinical features, local and systemic immune response, gastric mucosal histology, and gastric juice ascorbic acid concentrations" *Gut* (1991) vol. 32, pp. 1415–1418.

Sobala et al. "Ascorbic Acid In The Human Stomach" *Gastroenterology* (1989) vol. 97, pp. 357–363.

Steer "Surface morphology of the gastroduodenal mucosa in duodenal ulceration" *Gut* (1984) vol. 25, pp. 1203–1210.

Steffen et al. "abstract No. 1623" *Biological Abstracts* (1986) vol. 82, No. 1626 [abstract only].

Steinhoff et al. "Bismuth Subsalicylate Therapy of Viral Gastroenteritis" *Gastroenterology* (1980) (Jun. 1980) vol. 78, No. 6, pp. 1495–1499.

Stolte "Helicobacter pylori: Auch ein Krebserreger?" *GASTRO–LIGA Report* (Mar./Apr. 1994) pp. 5–7 [in German].

Stolte "Helicobacter pylori–syndrom: von der gastritis bis hin zum malignom" (Mai 1992) pp. 3–10 [in German].

Sutton. "Gastric ulcer healing with tripotassium dictrato bismuthate and subsequent relapse" *Gut* vol. 23 (1982), pp. 621–624.

Tiomny et al. "Halitosis and helicobacter pylori" *J. Clin. Gastroenterol.*, (1992) vol. 15, No. 3, pp. 236–237.

Tytgat et al. "DE–NOL® in the treatment of peptic ulcer. Proceedings of the DE–NOL® symposium" *Scand J of Gastroenterology* (Jun. 15, 1982), pp. iv–61.

Wagner et al. "Bismuth subsalicylate in the treatment of $H_2$ blocker resistant duodenal ulcers: role of Helicobacter pylori" *Gut* (1992) vol. 33, pp. 179–183.

Wallace. ed. "Can Germs Cause Gastritis and Ulcers?" *Harvard Medical School Health Letter*, (Nov. 3, 1987), pp. 2–4.

Warren, J. with reply from B. Marshall "Unidentified Curved Bacilli on Gastric Epithelium in Active Chronic Gastritis" *The Lancet* (Jun. 4, 1983) vol. 1 pp. 1273–1275.

Wieriks et al. Pharmacological Properties of Colloidal Bismuth Subcitrate (CBS, DE–NOL®) *Scand. J. Gastroenterol.*, (1982), vol. 17, supp. 80, pp. 11–16.

Wormsley "Relapse of duodenal ulcer" *British Medical Journal* (Dec. 6, 1986) vol. 293, p. 1501 [letter only].

Wu et al. "Platelet–derived Growth Factor–BB Accelerates Wound Closure in a New Mesenter Culture Model Without Macrophages" *Annals of Plastic Surgery* (Aug. 1994), vol. 33, No. 2, pp. 155–161.

Zhang et al. "Protective Effects of Furazolidone and Some Commonly Used Antiulcer Drugs on Several Gastric Ulcer Models in Rats" *Yaoxue Xuebao* (1984) vol. 19, pp. 5–11.

Zheng et al. "Double–blind Short–term Clinical Trial of the Effect of Furazolidone in Peptic Ulcer" *Chinese J. of Int. Medicine* (1984) vol. 23, pp. 195–197.

Zheng et al. "Double–blind Short–term Trial of Furazolidone in Peptic Ulcer" *The Lancet* (1985) vol. 1, pp. 1048–1049.

Zheng et al. "Treatment of Gastrointestinal Ulcer by Furazolidone" *Chinese J. of Digestion* (1982) vol. 2, pp. 131–133.

Drumm et al. "Association of Campylobacter Pyroli on the Gastric Mucosa With Antral Gastritis in Children" *The New England Journal of Medicine* (Jun. 18, 1987), vol. 316, No. 25, pp. 1557–1599.

Tytgat et al. "Campylobacter pylori Diagnosis and Treatment" *Journal Clinical Gastroenterol*, vol. ii, Suppl. 1, 1989, pp. S49–S53.

Tytgat et al. "Helicobacter pylori: Casual agent in peptic ulcer disease?" *Working Party Reports*, (1990) pp. 36–45.

Piper, "Bactria, gastritis, acid hyposecretion and peptic ulcer" *The Medical Journal of Australia*, vol. 142, Apr. 15, 1985, p. 431.

Lambert et al. "Effect of Colloidal Bismuth (De–Nol) on Healing and Relapse of Duodenal Ulcers—Role of Campylobacter Pyloridis", Abstract No. 91, IVth International Workshop of Campylobacter Infections, Goteberg, Sweden, June, 1987, p. 383.

Goodwin et al. "Clearance of Campylobacter pylori and reduced duodenal ulcer relapse with bismuth and tinidazole compared to cimetidine", Abstract No. 60, IVth International Worshop on Campylobacter Infections, Goteberg, Sweden, Jun. 1987, pp. 368–369.

Malfertheiner et al. "Chronic Erosive Gastritis—a Therapeutic Approach with Bismuth", *Scandinavian Journal of Gastroenterology*, vol. 23, Supp. 142, 1988, pp. 87–92.

"Wismut", XV 3, pp. 789–791.

Goodwin et al. "Transfer of Campylobacter pylori and Campylobacter Mustelae to Helicobacter gen. nov. as Helicobacter pylori comb. nov. and Helicobacter mustelae comb. nov., Respectively", *International Journal of Systematic Bacteriology*, Oct. 1989, vol. 39, No. 4 pp. 397–405.

Medline Abstract of: Lambert, J. R.; Dunn, K.; Borromeo, M.; Korman, M. G. "Campylobacter pylori—a role in non–ulcer dyspepsia?"; *Scandinavian Journal of Gastroenterology. Supplement* (1989), 160, 7–13, one page.

CA Abstract AN 1993:421501 of: Nguyen, A. M. H.; Engstrand, L.; Genta, R. M.; Graham, D. Y.; El–Zaatari, F. A. K. "Detection of Helicobacter pylori in dental plaque by reverse transcription–polymerase chain reaction"; *J. Clin. Microbiol.* (1993), 31(4), 783–7, one page.

McLean et al. "Microbes, Peptic Ulcer, and Relapse Rates with Different Drugs," *The Lancet*, Sep. 1, 1984, pp. 525–526.

Morris, A.; Brown, P.; Ali, M. R.; Lane, M.; Palmer, R. "Treatment of Campylobacter pylori gastritis: a pilot study using pirenzepine dihydrochloride (Gastrozepin) and three formulations of colloidal bismuth subcitrate (De–Nol)", The New Zealand Medical Journal, Oct. 26, 1988, vol. 101, No. 856, part 1, pp. 651–654.

Derwent Abstract No. XP–002176392 of Japanese Patent Application 08 020543, Jan. 23, 1996 (Inventor Narayan K. Athanikar).

METHOD OF MAKING CHEWING GUM CONTAINING COLLOIDAL BISMUTH SUBCITRATE

This application is a continuation of application Ser. No. 09/072,523, filed May 4, 1998, now U.S. Pat. No. 6,258,376, which is hereby incorporated by reference herein.

This application is a continuation-in-part of application Ser. No. 08/741,781, filed Nov. 1, 1996, now U.S. Pat. No. 5,834,002, incorporated herein by reference, which is a continuation-in-part of application Ser. No. 08/385,060, filed Feb. 7, 1995 now abandoned.

BACKGROUND OF THE INVENTION

This invention relates to chewing gum compositions containing active ingredients. More particularly, this invention relates to producing chewing gums that contain compounds for treating ulcers and halitosis.

Chewing gum compositions, typically, include a water soluble bulk portion, a water insoluble chewing gum base portion and water insoluble flavoring agents. Also, chewing gum compositions can be formulated to provide the delivery of active agents. These active agents may be a variety of breath fresheners, or medicaments, such as laxatives, aspirin or nicotine. Delivering these medicaments through a chewing gum vehicle is desirable for people who have difficulty swallowing pills. Also, the bad taste of some of the agents may be disguised by stronger flavoring agents in the chewing gum, which may make gum a suitable vehicle for delivery of certain medicines. Moreover, some medicines may be absorbed directly into the bloodstream through the tissue lining the mouth, making the medicine more readily available than if absorbed through the gastrointestinal walls. Accordingly, many people can benefit from new discoveries of how to effectively deliver active ingredients through a chewing gum formulation.

Unfortunately, many active ingredients are not suitable for administration through a chewing gum for a variety of reasons. A chewing gum cannot be effective if it has unpleasant medicinal taste, causes discoloration in the user's mouth, or the active ingredient causes poor chewing characteristics. A chewing gum cannot be effective if the active ingredient is not readily released from the gum, and thus, not delivered either into the mouth or the stomach where it can be absorbed or act topically. For this reason, many active ingredients may be effectively delivered by chewable tablets, or swallowable tablets, but not by chewing gum.

Recent discoveries have associated bacterial infection in the causation of peptic ulcer disease. The bacterium found to be associated with peptic ulcers has been identified as *Helicobacter pylori*. Excessive gastric acidity and mental stress are no longer thought to be the major pathophysiological reasons for the occurrence of peptic ulcers. Thus, questions regarding the previously established paradigms of and approaches for ulcer treatment and healing processes have been raised.

Previously, ulcers were treated by suppressing secretion of acid in the stomach. H2-receptor blockers, such as cimetidine (Tagamet®) and Ranitidine (Zantac®), suppress acid secretion and have been used to treat and heal duodenal ulcers. However, these H2-receptor blockers do not eliminate the *Helicobacter pylori* bacteria ("*H. pylori*"). These drugs do not reverse the tendency for ulcers to form.

For many years bismuth compounds have been used in swallowable tablet form and liquid form for treating ulcers. The therapeutic efficacy of bismuth compounds such as colloidal bismuth subcitrate, CBS, (also known as tripotassium dicitrato bismuthate), in healing duodenal ulcers and lowering relapse rates is attributed to its specific antibacterial activity against *H. pylori*. However, using bismuth compounds alone, *H. pylori* eradication rates of about 10 to 40% has been reported. Also, patients would suffer a relapse of ulcers after discontinuing taking the bismuth compounds.

Even though, as a single agent, CBS is significantly more effective in eradicating *H. pylori* than many other antibiotics, multiple therapies of bismuth compounds combined with other antibiotics have been reported to result in more than a 95% eradication rate for *H. pylori* and reduced ulcer relapse rate to less than 10% during a twelve-month follow-up period. For example, one such common triple therapy, comprised of CBS, amoxicillin and metronidazole, has been reported to have a high rate of effectiveness. However, it would be desirable to achieve such effectiveness in eradicating *H. pylori* with simple single agent therapies. No such single agent heretofore has been shown to be effective.

SUMMARY OF THE INVENTION

The present invention, therefore, is related to development of a chewing gum formulation to effectively eradicate *H. pylori* colonies without the need for combination antibiotic therapies. This invention is related to a chewing gum formulation containing a water soluble bulk portion, a water insoluble chewing gum base portion, a flavoring agent, and compounds selected from the group consisting of colloidal bismuth subcitrate, bismuth citrate, bismuth subcitrate, bismuth salicylate, bismuth subsalicylate, bismuth subnitrate, bismuth subcaibonate, bismuth tartrate, bismuth subgallate, bismuth aluminate, and combinations thereof This chewing gum has been found to eradicate or reduce *H. pylori* in reservoirs in the oral cavity and at the cite of infection and ulceration in the gastric mucosa. The invention further provides for a method of treating *H. pylori* infection by the administration of a chewing gum containing an amount of bismuth in a bismuth-containing compound equivalent to between about 10 and 200 milligrams of colloidal bismuth subcitrate. The invention further provides for the method of treating halitosis by the administration of a chewing gum containing bismuth compounds.

DETAILED DESCRIPTION OF THE INVENTION

In general, chewing gum compositions include a water soluble bulk portion, a water insoluble chewing gum base portion and, typically, water insoluble flavoring agents. The water soluble portion dissipates with a portion of the flavoring agents over a period of time during chewing. The gum base portion is retained in the mouth throughout the chewing process.

The insoluble gum base generally includes elastomers, resins, fats, oils, waxes, softeners and inorganic fillers. The elastomers may include polyisobutylene, isobutylene-isoprene copolymer, styrene butadiene rubber and natural latexes such as chicle. The resins may include polyvinyl acetate and terpene resins. Low molecular weight polyvinyl acetate is a preferred resin. Fats and oils may include animal fats such as lard and tallow, vegetable oils such as soybean and cottonseed oils, hydrogenated and partially hydrogenated vegetable oils, and cocoa butter. Commonly used waxes include petroleum waxes such as paraffin and microcrystalline wax, natural waxes such as paraffin and microcrystalline wax, natural waxes such as beeswax, candellia, carnauba and polyethylene wax. Preferably, the waxes have a melting point between 95° F. and 240° F.

The gum base typically also includes a filler component such as calcium carbonate, magnesium carbonate, talc, dicalcium phosphate and the like; elastomers, including glycerol monostearate and glycerol triacetate; and optional ingredients such as antioxidants, colors and emulsifiers. The gum base constitutes between 5 and 95% by weight of the chewing gum composition, more typically 10–50% by weight of the chewing gum, and commonly 25–35% by weight of the chewing gum.

The water soluble portion of the chewing gum may include softeners, bulk sweeteners, high intensity sweeteners and combinations thereof. Softeners are added to the chewing gum in order to optimize the chewability and mouth feel of the gum. The softeners, which are also known as plasticizers or plasticizing agents, generally constitute between about 0.5–15% by weight of the chewing gum. The softeners may include glycerin, lecithin, and combinations thereof. The softeners may also include aqueous sweetener solutions such as those containing sorbitol, hydrogenated starch hydrolysates, corn syrup and combinations thereof.

Bulk sweeteners constitute between 20–80% by weight of the chewing gum and may include both sugar and sugarless sweeteners and components. Sugar sweeteners may include saccharide containing components including but not limited to sucrose, dextrose, maltose, dextrin, dried invert sugar, fructose levulose, galactose, corn syrup solids, and the like, alone or in combination. Sugarless sweeteners include components with sweetening characteristics but are devoid of the commonly known sugars. Sugarless sweeteners include but are not limited to sugar alcohols such as sorbitol, mannitol, xylitol, hydrogenated, starch hydrolysates, maltitol, and the like, alone or in combination.

High intensity sweeteners may also be present. These may include but are not limited to sucralose, aspartame, salts of acesulfame, alitame, saccharin and its salts, cyclamic acid and its salts, dihydrochalcones, thaumatin, monellin, and the like, alone or in combination.

Combinations of sugar and/or sugarless sweeteners may be used in chewing gum. The sweetener may also function in the chewing gun in whole or in part as a water soluble bulking agent. Additionally, the softener may also provide additional sweetness such as with aqueous sugar or alditol solutions.

One or more flavoring agents are generally present in the chewing gum in an amount within the range of about 0.1–10% by weight of the chewing gum, preferably between about 0.5–3% by weight of the chewing gum. The flavoring agents may include essential oils, synthetic flavors or mixtures thereof including but not limited to oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorally acceptable fashion. All such flavors and flavor blends are contemplated by the present invention.

Optional ingredients such as colors, such as titanium dioxide and the like, emulsifiers and pharmaceutical agents may also be included in chewing gum.

The active pharmaceutical agents in this chewing gum formulation of this invention include non-H-2 antagonist bismuth compounds. These bismuth compounds include colloidal bismuth subcitrate (CBS), bismuth citrate, bismuth subcitrate, bismuth salicylate, bismuth subsalicylate, bismuth subnitrate, bismuth subcarbonate, bismuth tartrate, bismuth subgallate, and bismuth aluminate.

Preferably, the bismuth compound is selected from Colloidal Bismuth Subcitrate (CBS), bismuth subcitrate, bismuth subsalicylate and their combination. Most preferably, the bismuth compound is Colloidal Bismuth Subcitrate (CBS). The structural formula of CBS is:

[Bi(OH)$_3$]$_5$BiC$_6$H$_6$O$_7$ (1,2,3-PROPANETRICARBONIC ACID, 2-HYDROXY, BISMUTH(3 T)POTASSIUM); CAS#57644-54-9

Colloidal bismuth subcitrate and other bismuth compounds may be coated, micro-encapsulated, or agglomerated before incorporating in the chewing gum formulation to further cause the slow dissolution and sustained concentration of the compounds in the saliva. The polymers used for coating or encapsulation may include methylcellulose, carboxymethylcellulose, hydroxy-propylmethylcellulose, ethylcellulose, carbowax, polyethyleneglycols, acrylic polymers, to name a few. For example, CBS can be coated with a coating solution containing hydroxy-propylcellulose and polyethylene glycol in hydro-alcoholic solvent employing a fluid-bed coating equipment. The coated CBS particles should be assayed for CBS content and dissolution characteristics.

It is preferred that the chewing gum formulation containing bismuth compounds be capable of releasing the drug in a precise and reproducible fashion during a fifteen-minute chewing time. Preparing the bismuth compound using any of the above techniques may achieve such uniform release.

The chewing gum formulations may also include anti-plaque agents. The anti-plaque agents further contribute to improved efficacy by breaking down the plaque and exposing the H. pylori bacterial colonies to the anti-bacterial agents. Anti-plaque agents include, but are not limited to, glucanase anhydroglucosidase, glucose oxidase, calcium kaolin, silicone oil, sanguinarine, and the like.

Optionally, an antibiotic, such as metronidazole, can be added to the chewing gum formulation to broaden the anti-microbial activity against H. pylori. However, a preferred form of the chewing gum comprises an active pharmaceutical agent that consists essentially of a bismuth compound selected from the group consisting of colloidal bismuth subcitrate (CBS), bismuth citrate, bismuth subcitrate, bismuth salicylate, bismuth subsalicylate, bismuth subnitrate, bismuth subcarbonate, bismuth tartrate, bismuth subgallate, and bismuth aluminate.

Chewing gum is generally manufactured by sequentially adding the various chewing gum ingredients to any commercially available mixer known in the art. Generally, the ingredients are mixed by first melting the gum base and adding it to the running mixer. The gum base may alternatively be melted in the mixer. Color and emulsifiers can be added at this time. A softener such as glycerin can be added next along with syrup and part of the bulk portion. Further parts of the bulk portion may then be added to the mixer. The flavoring agent, pharmaceutical agent, and other optional ingredients of this ilk, are typically added with the final part of the bulk portion. The entire mixing process typically takes from five to fifteen minutes, although longer mixing times are sometimes required. Those skilled in the art will recognize that variations of this mixing procedure, or other mixing procedures, may be followed.

After the ingredients have been thoroughly mixed, the gum mass is discharged from the mixer and shaped into the desired form such as by rolling into sheets and cutting into sticks, extruding into chunks, or casting into pellets. Pellet or ball gum is prepared as conventional chewing gum, but formed either into pellets that are pillow-shaped or into balls. The pellets/balls can then be coated or panned by conventional panning techniques to make a unique sugar-coated pellet gum. Conventional panning procedures generally apply a liquid coating to a pellet, which is then solidified, usually by drying the coating. The hard-shell coating layer is built up by successive coating and drying steps.

Conventional panning procedures generally coat with sucrose, but recent advances in panning have allowed the use of other carbohydrate materials to be used in the place of sucrose, yet still obtain a hard-shell coating. Some of these components include, but are not limited to, dextrose, maltose, xylitol, lactitol, palatinit and other new alditols or a combination thereof These materials may be blended with panning modifiers including, but not limited to, gum arabic, maltodextrins, corn syrup, gelatin, cellulose type materials like carboxymethyl cellulose or hydroxymethyl cellulose, starch and modified starches, vegetable gums like alginates, locust bean gum, guar gum, and gum tragacanth, insoluble carbonates like calcium carbonate or magnesium carbonate, and talc. Antitack agents may also be added as panning modifiers, which allow the use of a variety of carbohydrates and sugar alcohols to be used in the development of new panned or coated gum products. Flavors may also be added with the sugar coating and with the bulk sweetener to yield unique product characteristics.

The chewing gum formulation of the present invention is superior to conventional therapy for treating ulcers. It turns out that the conventional bismuth therapy was shown to be only somewhat effective in eliminating *H. pylori* from the gastric mucosa, but had no effect on the *H. pylori* colonies in dental plaque. Colloidal bismuth subcitrate (CBS), an effective agent against *H. pylori*, however, is not absorbed significantly from the gastrointestinal tract, and therefore produces insufficient salivary concentrations through systemic recycling to affect *H. pylori* in the mouth. This continued presence of *H. pylori* in the dental plaque, and possibly the throat and esophagus, raises the question of whether the relapse of ulcers was inevitable with conventional bismuth therapy.

Multiple therapies of bismuth compounds combined with other antibiotics have been found to be superior to conventional bismuth therapy. Typical combinations include bismuth subsalicylate, metronidazole and amoxicillin or tetracycline. One possible explanation for the observed clinical efficacy of the antibiotic and bismuth combination that has not been advanced by the scientific community is that the metronidazole is actively secreted in the saliva where it may be exerting anti-microbial action against dental plaque-bound *H. pylori* colonies that the bismuth compounds administered alone in swallowable tablets cannot reach.

Interestingly, the antibiotics administered as single agents were only partially effective. Even though metronidazole is secreted in the saliva and may eradicate *H. pylori* in the mouth, it is not effective in single-handedly eradicating *H. pylori* in the gastric mucosa, i.e., the stomach. Therefore, assuming this explanation is correct, it is reasonable to believe that in order to achieve nearly complete eradication of *H. pylori*, and prevent relapses of ulcers, it is essential to eradicate the bacterium from the oral cavity, and possibly the throat and esophagus, as well as from the gastric mucosa.

However, it was not known whether bismuth compounds would be therapeutically effective in the oral cavity. In prior use of CBS against ulcers, it was known that CBS undergoes conversion to bismuth trioxide under the influence of gastric acids in the stomach. Conventional wisdom accepted that bismuth trioxide was the active product in the eradication of duodenal *H. pylori*. Therefore, it was not expected that CBS in a chewing gum would show efficacy in eradicating *H. pylori* in the mouth. Moreover, it was not known at what dose levels bismuth compounds would provide therapeutic effectiveness, if at all, for topical use in the mouth.

Chewing gum formulations in this invention have since been shown to be therapeutically effective in clinical studies. Preferably, the chewing gum releases enough bismuth into saliva for eradication of *H. pylori* in the oral cavity. The minimum inhibitory concentration (MIC) of bismuth for *H. pylori* varies for each bismuth compound. For instance, it is established that the MIC of CBS for *H. pylori* is 8 μg/mL, and its range is 4 to 32 μg/mL.

Therefore, to ensure its effectiveness, the chewing gum formulation preferably releases bismuth into saliva up to at least 2 times the MIC, preferably a minimum of 2 to 10 times the MIC, most preferably 2 to 250 times the MIC. To achieve these concentrations in the saliva, the bismuth content per dosage of chewing gum can be between about 3.5 mg and about 75 mg, preferably between about 3.5 mg and about 37 mg, more preferably between about 9 mg and about 28 mg. The amount of bismuth-containing compound per dosage thus is determined by the bismuth content of that particular compound. For instance, each piece of CBS-containing chewing gum may contain between about 10 mg and about 200 mg of CBS, preferably between about 10 mg and about 100 mg, and more preferably between about 25 mg and about 75 mg. Accordingly, each piece of gum may include amounts of other bismuth compounds that provide the same bismuth equivalent as the aforementioned ranges of CBS.

Of course, the amount of bismuth compound in each piece may be halved so that a person would chew on two pieces at a time to have the same effective amount of bismuth. Also, the chewing gum should be chewed multiple times throughout the day to prevent the *H. pylori* colonies from returning to their original size. Preferably, the chewing gum will be administered in sequential doses of between one and ten times per day, more preferably between two and six times per day. Also, the chewing gum administered may comprise an active pharmaceutical agent that consists essentially of a bismuth compound selected from the group consisting of colloidal bismuth subcitrate (CBS), bismuth citrate, bismuth subcitrate, bismuth salicylate, bismuth subsalicylate, bismuth subnitrate, bismuth subcarbonate, bismuth tartrate, bismuth subgallate, and bismuth aluminate and combinations thereof.

In another embodiment of the present invention the chewing gum containing a previously described bismuth compound is administered simultaneously (or concomitantly) with a peroral dosage form, such as a swallowable tablet, containing a previously described bismuth compound.

The bismuth compound contained in the swallowable tablet used for concomitant treatment in accordance with this embodiment of the present invention may be the same as that of the chewing gum that is administered by itself. The bismuth content of the swallowable tablet can be equivalent to between about 300 mg–1200 mg of colloidal bismuth subcitrate per day, preferably. The concomitant treatment can be administered once or twice per day, more preferably once per day.

A wide range of changes and modifications to the embodiments of the invention described above will be apparent to persons skilled in the art. The following examples are not to be construed as imposing limitations on the invention, but are included merely to illustrate preferred embodiments.

EXAMPLE 1

Preparation of Active Agent

To an aqueous solution of ammonia are added bismuth citrate, citric acid, and caustic potash in specific stoichiometric proportions, and at specific temperatures. The solution is examined for turbidity and, if required, additional volume of ammonia solution is added to render the solution clear. The solution is then filtered on a carbon bed and spray dried to obtain free-flowing powder material. The product is packaged in an air and moisture proof glass container.

EXAMPLE 2

Preparation of Chewing Gum

A brief general description of the chewing gum is set forth as follows. Fully melt the gum base (at approximately 90° C.) in Bartender mixer, a jacketed mixer with sigma blades. Remove the hot water from the mixer jacket, allow to cool, and add lecithin and mix well. Cool further to approximately 50° C., and add liquid flavor and mannitol. Mix until uniform. Dry blend colloidal bismuth subcitrate in sorbitol, and blend sodium citrate in sorbo syrup. Add sorbitol and sorbo syrup blends to the gum base. Cool the product to 35° C., add flavor and sweetener and mix until smooth. Remove the product from the mixing kettle, roll to form a sheet of uniform thickness and score to produce chewing gum sticks weighing 2.5 g each. Wrap individual gum sticks in aluminum foil and place in plastic bags.

EXAMPLE 3

Composition of CBS-Containing Gum

Two variations of 50 mg CBS gum were prepared as shown in Table 1 below. Both formulations used were identical with the exception that Formula-2 contained sodium citrate to impart a firmer texture, while Formula-1 did not.

EXAMPLE 4

Measurement of Release Rate of Bismuth into Saliva

Among six healthy human subjects, who gave informed consent, three chewed the CBS-containing gum with sodium citrate, and the other three chewed CBS-containing gum without sodium citrate. The subjects chewed the gum samples for a total of 15 minutes. Saliva samples were collected at time interval of 0, 1, 5, 10, and 15 minutes of chewing. The saliva samples were then submitted to an analytical laboratory for bismuth analysis. Results are shown in Table 2 below.

TABLE 2

IN VIVO SALIVARY CONCENTRATION OF CBS FROM THE CHEWING GUM

| Formula | chewing time (min.) | saliva vol. (mL) | conc of Bi (ppm) | conc of active CBS ($\mu$g/mL) | XMIC |
|---|---|---|---|---|---|
| formula-1 | 0 | 4.4 (±0.5) | | | |
| | 1 | 3.3 (±1.4) | 900.7 (±239.1) | 1270.3 (±334.7) | 148.7 (±42.0) |
| | 5 | 5.4 (±1.5) | 257.7 (±112.3) | 363.3 (±158.9) | 45.0 (±19.9) |
| | 10 | 4.9 (±1.3) | 28.0 (±5.0) | 40.0 (±6.6) | 5.0 (±1.0) |
| | 15 | 5.2 (±2.1) | 15.8 (±17.8) | 25.7 (±23.0) | 3.1 (±2.7) |
| formula-2 | 0 | 7.2 (±0.5) | | | |
| | 1 | 4.8 (±1.9) | 888.3 (±329.5) | 1257.0 (±464.5) | 156.3 (±58.0) |
| | 5 | 8.5 (±1.7) | 326.0 (±113.3) | 572.7 (±159.7) | 63.7 (±19.9) |
| | 10 | 7.5 (±3.4) | 30.0 (±9.5) | 42.3 (±13.6) | 5.0 (±1.7) |
| | 15 | 7.7 (±3.8) | 10.7 (±6.7) | 14.7 (±9.2) | 1.8 (±1.2) |

TABLE 1

FORMULATIONS OF THE GUM (APPROX. 2.5 gm A PIECE)

| Formula-1 | |
|---|---|
| CBS | 50.0 mg |
| Crystalline Sorbitol | 910.0 |
| Gum Base | 575.0 |
| Sorbitol Solution | 500.0 |
| Mannitol | 400.0 |
| Peppermint Oil | 25.0 |
| Spray Dried Peppermint | 12.5 |
| Grade t Lecithin | 10.0 |
| Aspartame | 10.0 |
| Sodium Citrate | 10.0 |
| Total: | 2502.5 mg |
| Formula-2 | |
| CBS | 50.0 mg |
| Crystalline Sorbitol | 910.0 |
| Gum Base | 575.0 |
| Sorbitol Solution | 500.0 |
| Mannitol | 400.0 |
| Peppermint Oil | 25.0 |
| Spray Dried Peppermint | 12.5 |
| Grade t Lecithin | 10.0 |
| Aspartame | 10.0 |
| Total: | 2492.5 mg |

Saliva samples were analyzed for elemental bismuth in ppm units. The results were then converted to $\mu$g of active CBS per mL of saliva, and also expressed as a multiple of minimum inhibitory concentration (MIC) of CBS for *H. pylori*. As can be seen from the results for formula-2, the salivary concentrations of CBS are about 156, 64, 5, and 1.8 times the MIC at 1, 5, 10 and 15 minutes, respectively. The constant bathing of the oral cavity from saliva containing sufficient concentration of CBS (2 to 5 times the MIC) for up to 15 minutes can be expected to further reduce the population of viable cells of *H. pylori*.

In a separate study in human subjects, a chewing gum formulation containing 50 mg CBS was demonstrated to produce salivary CBS levels several times the MIC (250, 75, 15, and 3 times the MIC at 1, 5, 10 and 15 minutes of chewing, respectively) for *H. pylori* during 15 minutes of chewing. The chewing gum formulation has also been shown to possess pleasant flavor and taste characteristics.

EXAMPLE 5

Sensory Analysis of Chewing Gum

Sensory characteristics of the chewing gum were evaluated by the subjects during the 15 minutes of chewing. Again, three subjects chewed the CBS gum containing sodium citrate and three subjects chewed the CBS gum without sodium citrate. A nine point rating scale was used to evaluate each category. The results are shown in Tables 3 and 4 below.

TABLE 3

RESULTS OF SENSORY ANALYSIS RATING OF CBS GUM WITHOUT SODIUM CITRATE
(Formula-1)

| SENSORY CHARACTERISTICS | CHEWING TIME | | | |
|---|---|---|---|---|
| | 1 MIN | 5 MIN | 10 MIN | 15 MIN |
| Overall Flavor | 6.3 | 6.0 | 5.3 | 5.0 |
| (0 = dislike extremely, | (±1.2) | (±1.0) | (±1.5) | (±1.0) |
| 8 = like extremely) | | | | |
| Flavor Intensity | 5.7 | 4.7 | 3.7 | 3.0 |
| (0 = none, 8 = very strong) | (±1.5) | (±1.2) | (±0.6) | (±1.0) |
| Chew Qualities | 6.0 | 6.0 | 5.3 | 5.0 |
| (0 = dislike extremely, | (±1.0) | (±1.0) | (±1.0) | (±1.0) |
| 8 = like extremely) | | | | |
| Unpleasant Aftertase | 0.0 | 0.0 | 0.0 | 0.0 |
| (0 = none, 8 = very strong) | (±0.0) | (±0.0) | (±0.0) | (±0.0) |
| Overall Qualities | 6.3 | 6.0 | 5.7 | 5.3 |
| (0 = dislike extremely, | (±1.2) | (±1.0) | (±1.2) | (±1.5) |
| 8 = like extremely) | | | | |

TABLE 4

RESULTS OF SENSORY ANALYSIS RATING OF CBS GUM WITHOUT SODIUM CITRATE
(Formula-1)

| SENSORY CHARACTERISTICS | CHEWING TIME | | | |
|---|---|---|---|---|
| | 1 Min. | 5 Min. | 10 Min. | 15 Min. |
| Overall Flavor | 6.7 | 5.7 | 4.7 | 4.7 |
| (0 = dislike extremely, | (±0.6) | (±1.5) | (±1.2) | (±1.2) |
| 8 = like extremely) | | | | |
| Flavor Intensity | 6.7 | 6.0 | 5.0 | 3.7 |
| (0 = none, 8 = very strong) | (±0.6) | (±0.0) | (±1.0) | (±1.5) |
| Chew Qualifies | 4.7 | 5.0 | 4.3 | 4.3 |
| (0 = dislike extremely, | (±2.1) | (±2.0) | (±1.5) | (±1.6) |
| 8 = like extremely) | | | | |

TABLE 4-continued

RESULTS OF SENSORY ANALYSIS RATING OF CBS GUM WITHOUT SODIUM CITRATE
(Formula-1)

| SENSORY CHARACTERISTICS | CHEWING TIME | | | |
|---|---|---|---|---|
| | 1 Min. | 5 Min. | 10 Min. | 15 Min. |
| Unpleasant Aftertase | 0.7 | 1.7 | 1.7 | 2.0 |
| (0 = none, 8 = very strong) | (±1.2) | (±2.1) | (±2.1) | (±2.0) |
| Overall Qualifies | 6.3 | 5.7 | 4.7 | 4.0 |
| (0 = dislike extremely, | (±0.6) | (±1.2) | (±1.2) | (±1.0) |
| 8 = like extremely) | | | | |

In general, there were no dramatic differences in the sensory analysis between the two formulas. The sensory panel clearly shows that both chewing gum formulations have a desirable level of flavor and taste, and cause a minimal unpleasant aftertaste after chewing.

EXAMPLE 6

Topical Safety

Topical safety was evaluated in the six volunteers for up to 60 minutes after administration of the gum. The subjects were asked to report any adverse effects such as discomfort or irritation in the oral cavity.

There were no reports of any discomfort or irritation in the oral cavity by any of the subjects at either the 15 or 60 minute post administration time periods.

EXAMPLE 7

Storage Stability Study

Samples of chewing gum containing 50 mg of CBS were wrapped individually in foil wrappers. The pieces of gum were then placed in foil laminate bags, sealed, and placed in storage. Storage conditions include 40° C. and room temperature (RT). The duration of the stability testing was 90 days. The results are shown in Tables 5–8 below.

TABLE 5

THREE MONTH STABILITY DATA
IN VIVO SALIVARY CONCENTRATIONS IN HUMAN SUBJECTS
OF CBS FROM THE 50 MG CBS CHEWING GUM

| TIME/ CONDITION | CHEWING TIME (min) | SALIVA VOLUME (mL) | CONC OF Bi (ppm) | CONC OF Bi ($\mu$g/mL) | CONC OF ACTIVE CBS ($\mu$g/mL) | X MIC |
|---|---|---|---|---|---|---|
| ZERO TIME | 0 | 4.2 (±1.6) | NA | NA | NA | NA |
| | 1 | 4.9 (±4.5) | 1937.3 (±753.5) | 1937.3 (±753.5) | 2729.0 (±1060.2) | 341.0 (±132.7) |
| | 5 | 6.4 (±3.1) | 437.0 (±152.1) | 437.0 (±152.1) | 615.7 (±214.5) | 77.0 (±26.9) |
| | 10 | 3.9 (±0.1) | 36.0 (±28.6) | 36.0 (±28.6) | 50.7 (±40.5) | 6.4 (±5.0) |
| | 15 | 4.5 (±1.3) | 5.0 (±4.6) | 5.0 (±4.6) | 7.0 (±6.6) | 0.9 (±0.8) |
| 3 MONTHS AT 40° C. | 0 | 5.6 (±1.4) | NA | NA | NA | NA |
| | 1 | 2.9 (±1.8) | 1922.3 (±511.8) | 1922.3 (±511.8) | 2710.0 (±791.9) | 338.6 (±90.3) |
| | 5 | 5.6 (±1.7) | 399.3 (±278.1) | 363.7 (±113.3) | 563.0 (±329.3) | 70.3 (±49.1) |
| | 10 | 5.3 (±1.4) | 25.7 (±11.4) | 30.0 (±9.5) | 362.0 (±160.5) | 45.4 (±20.1) |
| | 15 | 4.9 (±0.4) | 7.9 (±4.9) | 10.7 (±6.7) | 10.8 (±6.8) | 1.4 (±0.9) |
| 3 MONTHS AT ROOM TEMP. | 0 | 5.1 (±1.3) | NA | NA | NA | NA |
| | 1 | 4.1 (±1.5) | 1240.0 (±458.7) | 1240.0 (±458.7) | 1748.0 (±646.6) | 218.0 (±80.6) |
| | 5 | 7.2 (±2.3) | 518.7 (±118.7) | 518.7 (±118.7) | 731.3 (±167.6) | 91.0 (±21.8) |
| | 10 | 6.0 (±2.2) | 12.5 (±10.6) | 12.5 (±10.6) | 17.7 (±14.6) | 2.1 (±1.8) |
| | 15 | 5.6 (±1.6) | 4.5 (±2.2) | 4.5 (±2.2) | 6.0 (±2.6) | 0.7 (±0.3) | n = 3 for each group

TABLE 6

THREE MONTH STABILITY DATA
RESULTS OF SENSORY ANALYSIS RATING OF 50 MG CBS GUM

| | SENSORY CHARACTERISTIC | CHEWING TIME | | | |
|---|---|---|---|---|---|
| | | 1 Min. | 5 Min. | 10 Min. | 15 Min. |
| ZERO TIME | OVERALL FLAVOR | 6.7 (±0.6) | 6.3 (±0.6) | 5.3 (±0.6) | 5.3 (±0.6) |
| | FLAVOR INTENSITY | 6.3 (±1.2) | 5.3 (±1.2) | 4.0 (±1.0) | 4.0 (±1.0) |
| | CHEW QUALITIES | 6.7 (±0.6) | 6.3 (±0.6) | 5.7 (±0.6) | 5.3 (±0.6) |
| | UNPLEASANT AFTERTASTE | 0.0 (±0.0) | 0.0 (±0.0) | 0.0 (±2.1) | 0.0 (±0.0) |
| | OVERALL QUALITIES | 6.7 (±0.6) | 6.3 (±0.6) | 5.7 (±0.6) | 5.3 (±1.2) |
| 3 MONTHS AT 40° C. | OVERALL FLAVOR | 6.0 (±0.0) | 4.7 (±0.6) | 2.7 (±1.2) | 2.7 (±1.2) |
| | FLAVOR INTENSITY | 5.3 (±1.2) | 3.0 (±0.0) | 2.3 (±0.6) | 2.0 (±1.0) |
| | CHEW QUALITIES | 5.7 (±0.6) | 5.0 (±1.0) | 4.3 (±0.6) | 4.3 (±0.6) |
| | UNPLEASANT AFTERTASTE | 0.3 (±0.6) | 0.3 (±0.6) | 0.0 (±0.0) | 0.0 (±0.0) |
| | OVERALL QUALITIES | 6.0 (±0.0) | 4.3 (±0.6) | 2.7 (±0.6) | 2.3 (±0.6) |
| 3 MONTHS AT ROOM TEMP. | OVERALL FLAVOR | 6.3 (±0.6) | 6.3 (±0.6) | 5.3 (±0.6) | 4.3 (±0.6) |
| | FLAVOR INTENSITY | 5.7 (±1.5) | 5.3 (±1.5) | 4.3 (±1.5) | 4.0 (±1.7) |
| | CHEW QUALITIES | 6.0 (±1.0) | 6.0 (±1.0) | 5.3 (±0.6) | 4.3 (±0.6) |
| | UNPLEASANT AFTERTASTE | 0.0 (±0.0) | 0.0 (±0.0) | 0.0 (±0.0) | 0.0 (±0.0) |
| | OVERALL QUALITIES | 6.3 (±0.6) | 6.3 (±0.6) | 5.3 (±0.6) | 4.7 (±1.2) |

Note: n = 3 for each analysis
Rating Scale:
0 = dislike extremely, 9-like extremely for: Overall Flavor, Chew Quality, Overall Quality
0 = none, 9-like extremely for: Flavor Intensity
0 = none, 9 = very strong for: Unpleasant Aftertaste

TABLE 7

EXPONENTIAL REGRESSION DATA OF TIME VS SALIVARY
CONCENTRATIONS EXPRESSED AS MULTIPLES OF MIC

| | Initial Test Lot # CBS-50-CG-0001 | Stability Lot # CBS-50CG-0002 | | Clinical Lot # CBS-50CG-0003 |
|---|---|---|---|---|
| | | Zero Time | 3 mo./RT | 3 mo./40° C. | |
| A (intercept) | 240.0 | 563.1 | 575.7 | 422.3 | 446.5 |
| b (slope) | −0.339 | −0.432 | −0.361 | −0.448 | −0.426 |
| r (correlation coefficient) | 0.992 | 0.998 | 0.948 | 0.971 | 0.959 |
| K (pseudo first order rate constant) | −0.339 | 0.432 | 0.361 | 0.448 | 0.426 |
| $t_{0.5}$ (min.) | 2.04 | 1.60 | 1.92 | 1.55 | 1.63 |

Mean $t_{0.5}$ = 1.748 (±0.218)

TABLE 8

RELEASE OF CBS FROM THE CHEWING GUM AFTER
15 MINUTES OF CHEWING BY HUMAN SUBJECTS

| | Stability Lot # CBS-50CG-0002 | | | Clinical Lot # CBS-50CG-0003 |
|---|---|---|---|---|
| | Zero Time | 3 mo./RT | 3 mo./40° C. | |
| Mg CBS/2.5 g gum Before chewing (%) | 45.6 (100) | 44.5 (100) | 46.1 (100) | 46.2 (100) |
| Mg CBS/2.5 g gum After 15 min chewing (%) | 3.5 (7.6) | 4.0 (9.0) | 4.5 (9.8) | 3.8 (8.2) |

Mean % of CBS Remaining in the gum after 15 min of chewing = 8.6 (±1.0)

Each piece of the gum used for the stability study (one for zero-time, two for three months, total three) was from the same lot number. The results show that bismuth concentration remains stable over the tested time period.

EXAMPLE 8

Denture Material Exposure Study

An evaluation of CBS salivary concentration on various denture materials was conducted in order to test any potential staining effect of the CBS on denture materials. Artificial saliva was used. The results are reported at Table 9 below.

TABLE 9

THE COMPOSITION OF ARTIFICIAL SALIVA

| Ingredients | Concentration per Liter |
|---|---|
| Sodium Bicarbonate | 0.50 g |
| Sodium Phosphate, Dibasic Dihydrate | 0.85 g |
| Calcium Chloride | 0.44 g |
| Magnesium Chloride | 0.06 g |
| Potassium Chloride | 1.40 g |
| Sodium Carboxyl Methyl Cellulose | 2.00 g |
| Phosphoric Acid to adjust pH to 6.4 Distilled Water | QS |

The test saliva was prepared by dissolving 0.500 g of colloidal bismuth subcitrate in 100 mL of the above artificial saliva. 500 mL of artificial saliva at room temperature was placed in one of two identical glass jars with lids. In the other jar was placed 500 mL of the artificial saliva at room temperature containing 0.50% of CBS. In each of the jars the denture material block and a magnetic stirrer was placed. The jars were then placed on the magnetic platform and set to agitate at a minimum rate for four hours. The denture materials that were exposed to artificial saliva containing either CBS or placebo are listed in Table 10 below.

The four hour exposure of natural tooth and other denture materials to 0.5% CBS in artificial saliva with mild agitation did not cause any staining, discoloration, or changes in texture.

TABLE 10

DENTURE MATERIALS

1) Natural tooth with silver amalgam filling
2) Composite resin (used on anterior teeth for filling)
3) Denture base acrylic resin
4) Porcelain fused to metal
5) Partial denture metal frame
6) Acrylic tooth (artificial)
7) Natural tooth

EXAMPLE 9

Clinical Efficacy Data

An open label, placebo-controlled pilot clinical study in ten patients with initial positive response for *H. pylori* in the dental plaque has been initiated. Data from six patients (four patients treated with CBS 50 mg chewing gum six times-a-day and two patients treated with placebo chewing gum six times-a-day for fifteen days) has been obtained. The dental plaque samples from the patients were collected before treatment, at day 7 and at day 15 after treatment, and tested by microbiological culture and CLO test. The results are set forth in Tables 11A and 11B below:

TABLE 11A

TREATED GROUP (n = 4)

| | | CLO | DUR POSITIVE (HRS:MINS) | CUL-TURE | SIDE EFFECTS (Stain/Odor) |
|---|---|---|---|---|---|
| Pt 1 | Day 0 | + | 1:00 | + | NE |
| 30/M | Day 7 | + | 1:45 | -ve | — |
| | Day 15 | + | 1:30 | -ve | — |
| Pt 2 | Day 0 | + | 2:15 | + | NE |
| 42/M | Day 7 | + | 1:30 | NA | — |
| | Day 15 | + | 4:00 | -ve | — |
| Pt 3 | Day 0 | + | 2:30 | + | NIL |
| 31/M | Day 7 | + | 4:30 | NA | NIL |
| | Day 15 | + | 5:30 | NA | NIL |
| Pt 4 | Day 0 | + | 2:30 | NA | NIL |
| 29/F | Day 7 | + | 4:00 | NA | NIL |
| | Day 15 | + | 5:30 | NA | NIL |

Mean CLO response time after 15 days = 4.125 HR
PLACEBO (n = 2)

TABLE 11B

| | | CLO | DUR POSITIVE (HRS:MINS) | CULTURE | SIDE EFFECTS (Stain/Odor) |
|---|---|---|---|---|---|
| Pt 1 | Day 0 | + | 1:00 | NA | NIL |
| 26/M | Day 7 | + | 1:30 | NA | NIL |
| | Day 15 | + | 1:30 | NA | NIL |
| Pt 2 | Day 0 | + | 1:15 | NA | NIL |
| 28/M | Day 7 | + | 2:00 | NA | NIL |
| | Day 15 | + | 2:30 | NA | NIL |

NA = Not available
Mean CLO response time after 15 days = 2.0 HR
NE = Not evaluated (before chewing)

The data show that for patients treated with CBS 50 mg chewing gum and placebo chewing gum on day 15 the mean CLO response times are 4.125 hours and 2.0 hours, respectively. The longer CLO test response time for CBS 50 mg chewing gum group compared to the placebo chewing gum group is indicative of substantial reduction in *H. pylori* density in the oral cavity of the active treatment group.

EXAMPLE 10

Clinical Trial Data

The MERETEK UBT™ (urea breath test kit) from MERETEK Diagnostics, Inc. can be used to detect the presence of *H. pylori* in the stomach for the diagnosis of ulcers. To perform the test, the patient is given a liquid containing urea that is enriched with the carbon-13 isotope. *H. pylori* is a urease positive bacteria. If the carbon-13 isotope is present in heavy concentrations in later breaths, it signifies the presence of *H. pylori* in the stomach.

Duodenal ulcer patients with a positive urea breath test were randomized into active and placebo groups and entered into a 15-day clinical trial. These patients did not receive any antibiotic therapy during the clinical trial. The patients in the active group received gum containing 50 mg of colloidal bismuth subcitrate per piece. The patients in the placebo group received gum not containing colloidal bismuth subcitrate. The patients were further subdivided into high dose and low dose groups. The patients in the high dose group chewed gum 6 times per day and the patients in the low dose group chewed gum 2 times per day. After 15 days, the urea breath test was repeated. The results are reported in Table 12 below.

TABLE 12

UREA BREATH TEST RESULTS FROM 15-DAY CLINICAL TRIAL

| Subject Initials | Subject Group | Overall Assessment (Initial) | Overall Assessment* (Day 15) | Overall Change in Data** (Initial to Day 15) |
|---|---|---|---|---|
| A | high active | + | + | decrease 79% |
| B | high active | + | − | decrease 86% |
| C | high active | + | − | decrease 93% |
| D | high active | + | − | decrease 89% |
| E | high active | + | − | decrease 98% |
| F | high active | + | − | decrease 98% |
| G | low active | + | + | decrease 22% |
| H | low active | + | + | decrease 24% |
| I | low active | + | − | decrease 98% |
| J | low active | − | − | decrease 51% |
| K | low active | + | − | decrease 94% |
| L | low active | + | − | decrease 95% |
| M | high placebo | + | + | increase 42% |
| N | low placebo | + | + | increase 35% |
| O | low placebo | + | + | decrease 9% |

*Overall assessment is a qualitative result (either positive or negative) based on a numerical value established for the test.
**Overall change in data refers to the difference in numerical values from initial test to day 15.

Results of Overall Assessment
1. All three patients receiving placebo (100%) had positive urea breath tests at the conclusion of the trial.
2. Eight of eleven patients receiving active gum (73%) had negative urea breath tests at the conclusion of the trial.
3. One patient with negative results at the start (i.e., below threshold value to consider the test positive) was not included.

Results of Overall Changes in Data
1. The average change in urea breath test data was an increase of 23% in the three placebo patients.
2. The average change in urea breath test data was a decrease of 64% in the six patients on the low active dose (range of 22% to 98%).
3. Six of six patients in the low active drug group had a decrease (p<0.05 by chi-square analysis).
4. The average change in urea breath test data was a decrease of 91% in the six patients on the high active dose (range of 79% to 98%).

5. Six of six patients in the high active drug group had a decrease (p<0.05 by chi-square analysis).

Summary of Results

1. Twelve of twelve patients on active gum had decreases in urea breath test data results (ranging from 22% to 98%), whereas three placebo patients had an average increase of 23%).
2. There was a dose-response relationship between the two doses of gum used. The data suggest that the doses are near the peak of the dose-response relationship.
3. The data strongly suggest that *H. pylori* has been eradicated from the stomach by the active gum used in this clinical trial.

This study also further examined whether delivering CBS in the saliva over a period of time through chewing gum, which eventually is delivered in solution form to the stomach running down the entire GI track, will result in clearing *H. pylori* in the oral cavity as well as in the stomach. CBS chewing gum containing 50 mg of CBS per piece of gum was given to patients to chew at 2 and 6 times a day. A like group was given placebo chewing gum.

*H. pylori* presence in the oral cavity (dental plaque) was determined by RT-PCR, a technique that measures minute quantities of DNA that is matched with *H. pylori* specific markers. The dental plaque samples were collected on Day 0 (screening), Day 15 and Day 45 by following a pre-set sampling plan. The dental plaque samples were collected by a dentist.

Several published reports on the RT-PCR test have demonstrated that *H. pylori* is detected in the dental plaque on the average in 40% of the patients that had *H. pylori* in the stomach. This lower rate of detecting *H. pylori* in the dental plaque has been thought to be due to inadequate sampling of the dental plaque, even under reasonably extensive sampling plan. Therefore, a negative result for *H. pylori* RT-PCR test in the dental plaque has a high probability for false negative.

The results for the RT-PCR test for the dental plaque are shown in Table 13 below. In this test, 10/11(90.9%) patients in the low active-group, 5/8(62.5%) in the high-active group, and 7/8(87.5%) in the placebo group were negative for *H. pylori* in the dental plaque following two weeks of treatment. The high negative results for the placebo group may have been caused by inadequate plaque sampling. Additionally, the fluid dynamics caused by chewing action may have contributed for dislodging and/or plaque reduction, resulting in negative test in the dental plaque sample. Because of the reported inherent difficulty in dental plaque sampling, and little understood fluid dynamics of the plaque structure, the RT-PCR results are equivocal and inconclusive in establishing the efficacy of CBS chewing gum in reducing or eradicating *H. pylori* from the oral cavity.

TABLE 13

RT-PCR Test Results
Proportion of Patients with Negative Results for
*H. pylori* in the Dental Plague

| Visit | Active-Low | Active-High | Placebo | p-value[b] Active vs. Placebo | p-value[b] Active-Low vs. Active-High |
|---|---|---|---|---|---|
| Day 15[a] | 10/11 (90.0%) | 5/8 (62.5%) | 7/8 (87.5%) | 1.000 | 0.262 |

[a]Day 15 positive results were based on the RT-PCR dental plaque test being positive. Patients 5, 9, 10, 21, and 23 did not have test results at Day 15.
[b]p-value based on two-tailed Fisher's Exact Test. Patients 4, 29, and 30 were excluded from the analysis.

The study also considered the results of a urea breath test. As noted above, *H. pylori* is a urease-producing bacteria, and in the stomach it is capable of hydrolyzing urea to generate ammonia and carbon dioxide. Upon consumption of $^{13}C$ labeled urea pudding, $^{13}CO_2$ is produced in the stomach of patients with *H. pylori* infection. This $^{13}CO_2$ is exhaled in the breath. The MERETEK $^{13}C$ Urea Breath Test (UBT) utilizes a Gas Isotope Ratio Mass Spectrometer (GIRMS) for the measurement of the ratio of $^{13}CO_2$ to $^{12}CO_2$ in the breath samples. The UBT has been demonstrated to be very sensitive and reproducible in measuring active *H. pylori* infection in the stomach of patients.

When both UBT and RT-PCR being negative at the end of two week treatment is considered, 11/20(55%) of patients in the active treatment group and 0/7(0%) of patients in the placebo group met this criteria.

Table 14 below displays the post-hoc analyses of numeric scores for change and percent change from baseline for the $^{13}C$ Urea Breath Test results by treatment group. The overall p-value demonstrated that there were statistically significant differences at Day 15 in change (p=0.005) and percent change (p<0.001) from baseline between the treatment groups. The active high-dose treatment group showed a statistically significant difference (p<0.05) from placebo in change and percent change (−93.0%) from baseline at Day 15. The active low-dose treatment group showed a statistically significant difference from placebo in percent change from baseline (−70.3%). There was no statistically significant difference from placebo in change from baseline.

TABLE 14

Change and Percent Change from Baseline in $^{13}C$ Urea Breath Test Results by Treatment Group

| Visit | Active Low-Dose | | | Active High-Dose | | | Placebo | | | Kruskal-Wallis Test | |
|---|---|---|---|---|---|---|---|---|---|---|---|
| | Mean | SD | N | Mean | SD | N | Mean | SD | N | Statistic | p-value |
| Baseline | 17.20 | 14.68 | 11 | 28.28 | 21.37 | 9 | 22.68 | 16.95 | 7 | 1.28 | 0.527 |
| Day 15[a] | 5.59** | 9.48 | 11 | 2.16** | 3.36 | 9 | 19.63 | 14.39 | 7 | 10.36 | 0.006 |

TABLE 14-continued

Change and Percent Change from Baseline in $^{13}$C Urea Breath Test Results by Treatment Group

|  | Active Low-Dose | | | Active High-Dose | | | Placebo | | | Kruskal-Wallis Test | |
| --- | --- | --- | --- | --- | --- | --- | --- | --- | --- | --- | --- |
| Visit | Mean | SD | N | Mean | SD | N | Mean | SD | N | Statistic | p-value |
| Change | −11.61 | 8.77 | 11 | −26.12** | 20.03 | 9 | −3.05 | 8.01 | 7 | 10.64 | 0.005 |
| Percent Change | −70.3%** | 30.18 | 11 | −93.0%** | 7.10 | 9 | −2.3% | 34.76 | 7 | 14.42 | <0.001 |

*overall p-value
**Statistically significant difference from placebo, p < 0.05.
[a]Patients 9, 10, 21, 23 and 28 did not have test results at Day 15. Patients 4, 29, and 30 were excluded from the analysis.

More remarkable treatment effects were observed at the completion of the study when the UBT results at the end of two week treatments are compared to pre-study screening results. These 15 day UBT results are shown at Table 15 below.

TABLE 15

$^{13}$C Urea Breath Test Results for *H. pylori*
Proportion of Patients with Negative Tests for *H. pylori*

| Visit | Active Low-Dose | Active High-Dose | Placebo | p-value[b] Active vs. Placebo | p-value[b] Active Low-Dose vs. Active High-Dose |
| --- | --- | --- | --- | --- | --- |
| Day 15[a] | 6/11 (54.6%) | 8/9 (88.9%) | 0/7 (0.0%) | <0.002 | 0.157 |

[a]Day 15 positive results were based on the $^{13}$C Urea Breath Test being positive. Patients 9, 10, 21, 23, and 28 did not have results at Day 15
[b]p-value based on two-tailed Fisher's Exact Test. Patients 4, 29, and 30 were excluded from the analysis In the high-active (6 times a day) group, 8/9(88.9%) patients ware converted to negative UBT (score≦2.5) at the end of two week treatment (Day 15). Even the one patient that did not covert to negative, the UBT score was decreased by 79% from the base line score. An overall decrease of 93% in the UBT score from the base line was observed for the high-active group.

In the low-active group (2 times a day), 6/11(54.6%) were converted to negative UBT, and an overall 70% decrease in the UBT score from the base line was observed. The study has clearly demonstrated a dose dependent increase in the efficacy.

In the placebo group (both 6 and 2 times a day), 0/7 (0%) converted to negative UBT. In 4/7(57.1%) patients the UBT score at the end of two week treatment was higher than the base line score. An overall decrease of 3% in the UBT score from the base line was observed.

The 88.9% UBT conversion following two weeks treatment with CBS 50 mg chewing gum, 6 times a day dosing schedule, is highly remarkable in that the total daily dose is only 300 mg of CBS (equivalent to 120 mg of bismuth trioxide). In the hitherto reported clinical studies with 300 mg CBS oral tablets, two tablets 2 times a day (a total of 4 tablets or 1,200 mg CBS [equivalent to 480 mg of bismuth trioxide]) up to 4 weeks of treatment as a mono therapy, an average of 30 to 40% eradication rates are demonstrated. Although the different criteria have been used to determine eradication in those studies, a reasonable comparison still establishes a superior efficacy of CBS in the chewing gum delivery system.

One reason believed for this demonstrated increase in the CBS efficacy in the chewing gum delivery system could be that CBS dissolves in the saliva during the 15 to 20 minutes of chewing time. This results in significant concentration that bathes the oral cavity and eventually rinses down the entire GI tract. It has been demonstrated that, between one and five minutes of chewing, a CBS concentration from about 200 down to about 50 times the MIC for *H. pylori* develops in the oral cavity. This action may be eliminating/eradicating *H. pylori* that might be colonizing throughout the GI tract mucosal layer. Some evidence to this reasoning can be found in the demonstrated high efficacy of metronidazole and clarithromycin in the combination therapies. Both metronidazole and clarithromycin are secreted in the saliva extensively following oral absorption. The drug rich saliva bathes the oral cavity and also when eventually swallowed, rinses the entire GI tract mucosal layer, in a similar fashion to CBS in the chewing gum delivery system.

The symptoms of gastritis/dyspepsia and any type of scaling the symptoms was not required as the entry criteria. However, attempts were made to compare the symptoms at the end of the treatment to base line in a few patients. Since many patients were not severely symptomatic, the efficacy of the active treatment compared with the placebo is unequivocal. However, a slight trend in the reduction of Epigastric fullness is noticeable.

The results clearly demonstrate that a two week treatment with CBS 50 mg Chewing gum at 6 times a day dosing schedule as a mono therapy, eliminate *H. pylori* in the stomach as determined by UBT.

EXAMPLE 11

Antibacterial Efficacy for Treatment of Halitosis

Halitosis is caused by the buildup of Volatile Sulfur Compounds (VSC's). These VSCs arise from the breakdown of bacteria, tissue, and food particles trapped in the mouth. Other contributing factors include digestive problems, nose, throat and/or lung infections, and the intake of medications.

A halitosis meter can be used to detect the presence of bad breath. This meter uses an analyzer that can detect the levels of VSCs. Most individuals feel that odor is coming from their stomach, when really 80 percent originates from the mouth and tongue.

Typically, breath mints, chewing gum, mouth washes and toothpastes that you buy at the store merely mask your bad breath. These breath fresheners are only able to cover up the odor for a short time. In order to permanently eliminate bad breath it is necessary to attack the source of the VSCs.

*Campylobacter rectus, Helicobacter pylori*, and *Treponema denticola* are bacteria that have been demonstrated to be associated with Halitosis (bad breath). The bismuth-containing compounds and methods of the present invention, including CBS as well as ascorbyl bismuth derivative, have demonstrated in vitro activity against all three bacteria, as indicated by their minimum effective concentrations (MICs) presented in Table 16 below.

TABLE 16

| Test Organisms | Bismuth Ascorbyl Sulfate (µg/ml) | Bismuth Sucrose Sulfate (µg/ml) | CBS (µg/ml) |
|---|---|---|---|
| Canipylobacter rectus | 256 | >256 | 256 |
| Helicobacter pylori | 8 | 16 | 2 |
| Treponema denticola | 16 | 32 | 32 |

Based on the in vitro activity, a chewing gum containing CBS should be effective in reducing Halitosis caused by bacteria. It is expected that a person may treat halitosis by chewing gum containing preferably between about 10 mg CBS and about 100 mg CBS, and preferably between about one and four times per day. Also, the chewing gum may contain an a amount of bismuth in the aforementioned bismuth compound or combinations thereof equivalent to between about 10 and about 100 milligrams of colloidal bismuth subcitrate.

A study was conducted to evaluate a CBS 35 mg percent (0.035%) solution in reducing the oral bacterial count, and mal odor in human subjects upon rinsing (gargling) the mouth with 30 mL of this solution (Group I), compared with rinsing with 30 mL of distilled water (Group II).

All the subjects arrived at the study site in the morning without brushing their teeth. Each subject in Group I rinsed their mouth with 30 mL of CBS solution for one minute. The rinsing was collected into a sterile conical flask. The subjects then rinsed their mouth with 30 mL of sterile water for one minute, and the second rinsing was collected into a separate sterile conical flask.

Each subject in Group II rinsed their mouth with 30 mL of distilled water for one minute. The rinsing was collected into a sterile conical flask. The subjects then rinsed their mouth with 30 mL of sterile water for one minute, and the second rinsing was collected into a separate sterile conical flask.

One mL aliquot of each of rinsings I-A, II-A, I-B and II-B from all the subjects was plated on a growth media suitable for anaerobic bacteria, and incubated at suitable temperature for four days. The plates were examined for number of colonies and types of colonies after four days (96 hrs of incubation).

Comparisons were made between the CBS Group and Distilled Water Group for quantitative and qualitative differences in the colony count. The plates also were evaluated for presence of mal odor by olfactory test.

The results of bacterial colony counts and odor intensity are presented in the following Table 17.

TABLE 17

| Sample | Number of colonies | Organism types | Odor Intensity |
|---|---|---|---|
| Plate I-A | = 10* | Gram negative Coccobacilli | Undetectable |
| Plate I-B | = 10–20 | Gram negative Coccobacilli | Undetectable |
| Plate II-A | = 400–500 | Several different Gram negative & positive | Highly Offensive, Detectable from several feet from the open plates |
| Plate II-B | = 200–300 | Several different Gram negative & positive | Highly Offensive, Detectable from several feet from the open plates |

Notes:
*Only ONE of five plates
Plate I-A: First Rinse with 35 mg. Percent (0.035%) CBS Solution
Plate I-B: Second Rinse with Distilled Water
Plate II-A: First Rinse with Distilled Water
Plate II-B: Second Rinse with Distilled Water

EXAMPLE 12

Toxicology

A number of animal toxicity studies and human clinical investigations have demonstrated safety of bismuth compounds, especially CBS, in therapeutic dose ranges. No toxicity has been reported in chronic daily administration of high doses of CBS (160, 320, and 640 mg/kg body weight representing 2, 4, and 8 times the human therapeutic dose, respectively) in rats treated for three months or dogs treated for six months. See Wieriks et al., Journal of Gastroenterology 17(Supplement 80): 11B16 (1982), incorporated herein by reference.

Long term safety of CBS and treatment of peptic ulcers at a standard dose of 480 mg (expressed as bismuthtrioxide) in four daily divided doses has been examined by Bader, Digestion 37(Supplement 2):53–59 (1987), incorporated herein by reference. CBS was first introduced in Europe in 1971 and since that time 1.5 million treatments have been dispensed. During eight years of use of CBS tablets [De-Nol®] in Europe between 1978 and 1986 under a more comprehensive adverse reaction monitoring system, only 13 adverse reaction forms were completed. Five of these adverse reactions were ascribed to CBS: one case of headache, one case of stomach pain, one case of diarrhea, and two cases of allergy (mainly in the form of skin rashes). A high degree of safety of CBS in therapeutic applications for the treatment of peptic ulcers is reported in a review of pharmacology of bismuth-containing compounds by Lambert, Review of Infectious Diseases 13(Supplement 8):691–695 (1991), incorporated herein by reference. In reviewing safety and pharmacokinetics of CBS, Bennet, Scandinavian Journal of Gastroenterology 26 (Supplement 185):29–35 (1991), incorporated herein by reference, has calculated the systemic bioavailability of bismuth after oral dosing of CBS to be in the range of 0.16 to 0.28% of the administered dose, and concluded that steady-state blood levels of 50–100 ng/mL are unlikely to cause any neurotoxicity.

The safety of the Colloidal Bismuth Subcitrate (CBS) Chewing gum formulation containing 50 mg of CBS per piece of gum chewed at 2 and 6 times per day for two weeks was evaluated in comparison with placebo chewing gum. The systemic safety was accessed by blood chemistry and urinalysis. The laboratory values for individual patients were reviewed and no abnormalities related to the CBS gum were found.

There were no statistically significant differences in the incidence of reported adverse events between the active and placebo treatment groups. There were no discontinuation due to any adverse reactions.

The safety of the chewing gum in the oral cavity was assessed by a dentist. The tooth staining (oral cavity discoloration) potential was evaluated. Two patients in the 6 times per day CBS chewing gum group had slightly noticeable darkening of the tongue and gum margins, which diminished with brushing and rinsing. There were no darkening of the tongue or gum margins either in the 2 times per day CBS gum group or the placebo group.

There were no differences in the oral cavity irritation or inflammation measured by Gingival index between the treatment groups. However, oral cavity odor was less in the CBS chewing gum group compared to placebo chewing gum group, but the difference was not statistically different. There was no measurable difference in the Plaque index between any of the treatment groups.

The study demonstrates that CBS 50 mg chewing gum up to 6 times per day dosing for two weeks is systemically safe and does not cause any topical discomfort in the oral cavity.

It should be appreciated that the compositions and methods of the present invention are capable of being incorporated in the form of a variety of embodiments, only a few of which have been illustrated and described above. The invention may be embodied in other forms without departing from spirit or essential characteristics. The described embodiments are to be considered in all respects only as illustrative and not restrictive, and the scope of the invention is, therefore, indicated by the appended claims rather that the foregoing description. All changes which come within the meaning and range of equivalency of the claims are to be embraced within their scope.

What is claimed is:

1. A method of making a chewing gum for treatment of *H. pylori* in the oral cavity and gastric mucosa, the method comprising:
   a) providing a chewing gum base,
   b) providing a non-H2 antagonist bismuth compound, which is therapeutically effective against *H. pylori* in the oral cavity,
   c) mixing the chewing base and the non-H2 antagonist bismuth compound in sufficient proportions such that the amount of the non-H2 antagonist bismuth compound in a suitable serving size of chewing gum is therapeutically effective, and
   d) shaping the mixture into a desired product form;
      wherein the non-H2 antagonist bismuth compound is selected from the group consisting of colloidal bismuth subcitrate, bismuth citrate, bismuth subcitrate, bismuth salicylate, bismuth subsalicylate, bismuth subnitrate, bismuth subcarbonate, bismuth tartrate, bismuth subgallate, bismuth aluminate, bismuth ascorbyl sulfate, bismuth sucrose sulfate, and combinations thereof.

2. The method of claim 1, further comprising providing a flavoring agent, and mixing the flavoring agent into the chewing gum base.

3. The method of claim 2, further comprising providing a water soluble bulk portion, and mixing the water soluble bulk portion into the chewing gum base.

4. The method of claim 1, wherein the bismuth compound is selected from the group consisting of colloidal bismuth subcitrate, bismuth subcarbonate, bismuth tartrate, bismuth subgallate, bismuth aluminate, and combinations thereof.

5. The method of claim 4, wherein the bismuth compound is colloidal bismuth subcitrate.

6. The method of claim 1, wherein the chewing gum includes an amount of bismuth in said bismuth compound or combinations thereof equivalent to between about 10 mg and 200 mg of colloidal bismuth subcitrate per serving.

7. The method of claim 6, wherein the chewing gum includes an amount of bismuth in said bismuth compound or combinations thereof equivalent to between about 10 mg and about 100 mg of colloidal bismuth subcitrate per serving.

8. The method of claim 7, wherein the chewing gum includes an amount of bismuth in said bismuth compound or combinations thereof equivalent to between about 25 mg and about 75 mg of colloidal bismuth subcitrate per serving.

9. The method of claim 8, wherein the chewing gum includes an amount of bismuth in said bismuth compound or combinations thereof equivalent to about 50 milligrams of colloidal bismuth subcitrate per serving.

10. The method of claim 1, wherein the chewing gum further comprises an antibiotic.

11. The method of claim 10, wherein the antibiotic is metronidazole.

12. The method of claim 1, wherein the chewing gum further comprises an anti-plaque agent.

13. The method of claim 12, wherein said antiplaque agent is selected from gluconase and hydroglucosidase, glucose oxidase, calcium kaolin, silicone oil, and sanguinarine.

14. The method of claim 1, wherein no other compounds that are therapeutically effective against *H. pylori*, or for the treatment of ulcers, is included in the chewing gum.

15. The method of claim 1, wherein the chewing gum includes an amount of bismuth in said bismuth compound or combinations thereof equivalent to between about 0.4 weight percent and 8 weight percent of colloidal bismuth subcitrate.

16. The method of claim 15, wherein the chewing gum includes an amount of bismuth in said bismuth compound or combinations thereof equivalent to between about 0.4 weight percent and about 4 weight percent of colloidal bismuth subcitrate.

17. The method of claim 16, wherein the chewing gum includes an amount of bismuth in said bismuth compound or combinations thereof equivalent to between about 1 weight percent and about 3 weight percent of colloidal bismuth subcitrate.

18. The method of claim 17, wherein the chewing gum includes an amount of bismuth in said bismuth compound or combinations thereof equivalent to about 2 weight percent of colloidal bismuth subcitrate.

* * * * *